(12) United States Patent
Bixby et al.

(10) Patent No.: US 11,839,367 B1
(45) Date of Patent: Dec. 12, 2023

(54) APPARATUS AND METHOD OF TYING TISSUE TO BONE

(71) Applicant: RIVERPOINT MEDICAL, LLC, Portland, OR (US)

(72) Inventors: Elliot Bixby, Gladstone, OR (US); Edwin Anderson, Ridgefield, WA (US); Nathan Daniel Cook, Portland, OR (US); John Thomas Ferguson, Portland, OR (US)

(73) Assignee: Riverpoint Medical, LLC, Portland, OR (US)

( * ) Notice: Subject to any disclaimer, the term of this patent is extended or adjusted under 35 U.S.C. 154(b) by 322 days.

(21) Appl. No.: 17/387,854

(22) Filed: Jul. 28, 2021

Related U.S. Application Data

(60) Provisional application No. 63/057,711, filed on Jul. 28, 2020.

(51) Int. Cl.
  *A61B 17/04* (2006.01)
  *A61F 2/30* (2006.01)

(52) U.S. Cl.
  CPC ...... *A61B 17/0401* (2013.01); *A61F 2/30749* (2013.01); *A61B 2017/0414* (2013.01); *A61B 2017/0445* (2013.01); *A61F 2002/30751* (2013.01)

(58) Field of Classification Search
  CPC .. A61F 2/08; A61F 2/0811; A61F 2002/0852; A61B 17/0485; A61B 17/0401; A61B 2017/0406; A61B 2017/0409; A61B 2017/0477; A61B 17/04; A61B 17/06166; A61B 2017/0496; A61B 2017/06185; A61B 17/0469

See application file for complete search history.

(56) References Cited

U.S. PATENT DOCUMENTS

| | | | |
|---|---|---|---|
| 9,320,512 | B2 | 4/2016 | Dooney |
| 9,463,011 | B2 | 10/2016 | Dreyfuss |
| 9,504,462 | B2 | 11/2016 | Dooney |
| 10,058,322 | B2 | 8/2018 | Dooney |
| 10,070,856 | B1 | 9/2018 | Black et al. |
| 10,524,776 | B2 | 1/2020 | Dreyfuss |
| 11,076,844 | B2 | 8/2021 | Black et al. |
| 2015/0032157 | A1 | 1/2015 | Dooney |
| 2020/0178950 | A1 | 6/2020 | Burkhart |
| 2020/0205799 | A1 | 7/2020 | Burkhart |
| 2021/0196264 | A1* | 7/2021 | Bachmaier ....... A61B 17/06166 |

* cited by examiner

*Primary Examiner* — Katherine M Shi
(74) *Attorney, Agent, or Firm* — BrainSpark Associates, LLC

(57) ABSTRACT

A method of attaching target tissue to a pilot hole in a bone that utilizes a suture assembly having an anchor sleeve; a sliding suture, having a first end and a second end, and passing through the anchor sleeve; and a shuttle having a shuttle loop and a free end, opposed to the shuttle loop, and passing through the anchor sleeve, with the free end and the shuttle outside of the anchor sleeve. In the method, the sliding suture is passed about the target tissue and the first end is engaged to the shuttle loop. Then, the anchor sleeve is pushed into the pilot hole, and the free end is pulled to pull the shuttle into the anchor sleeve in the pilot hole, thereby setting the anchor sleeve into the pilot hole.

10 Claims, 17 Drawing Sheets

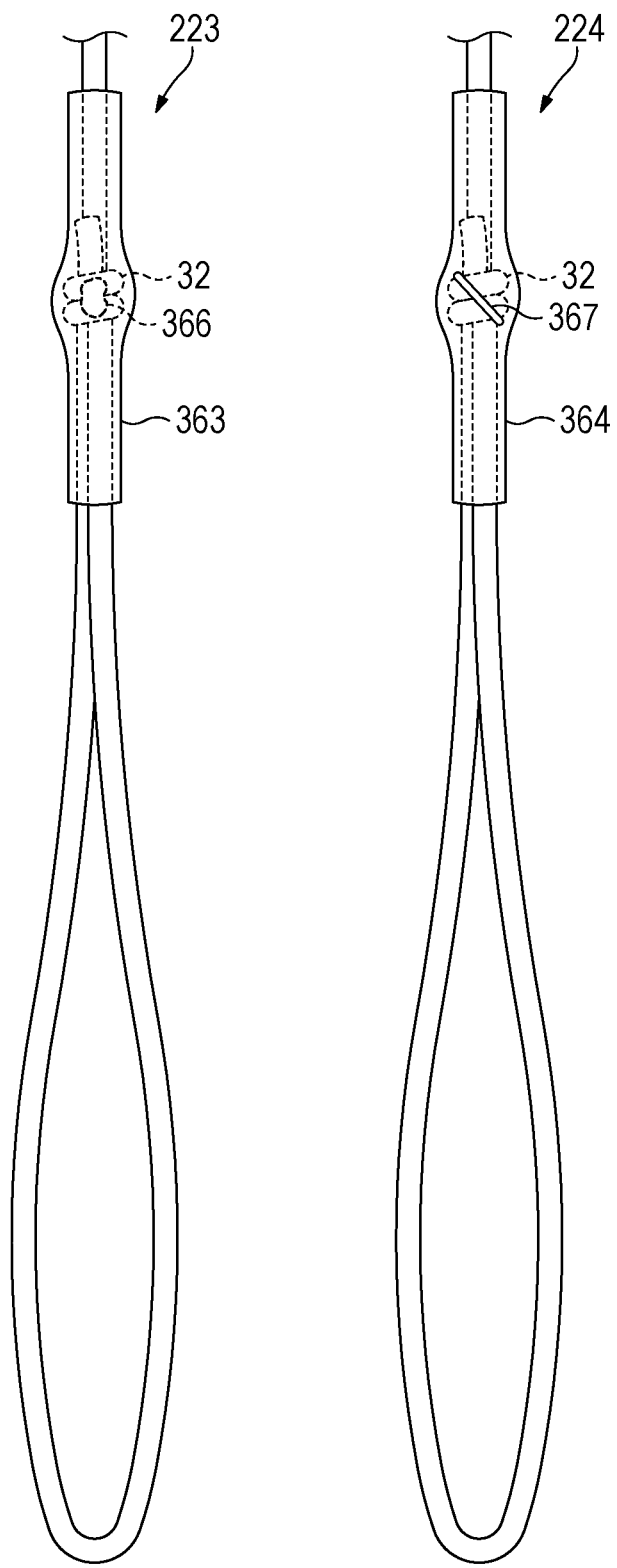
FIG. 10D  FIG. 10E

APPARATUS AND METHOD OF TYING TISSUE TO BONE

CROSS-REFERENCE TO RELATED APPLICATIONS

This application claims priority from Provisional Application Ser. No. 63/057,711, filed Jul. 28, 2020, which is incorporated by reference as if fully set forth herein.

BACKGROUND OF THE INVENTION

The labrum, the cup-shaped cartilage that lines and reinforces the glenoid (the bone defining the shallow shoulder socket), sometimes becomes torn or separates from the glenoid, thereby causing patient pain and limiting freedom of arm movement. To repair this tear or separation a number of methods are currently available to put a loop around a portion of the labrum, and to anchor that loop in the glenoid. It is typical to place three of these anchored loops along a portion of the labrum, to properly brace the labrum and/or reattach it to the glenoid.

Initially, placing these anchored loops along a portion of the labrum required tying a knot for each loop, and leaving the knot in the patient, which tended to slow healing from the operation. More recently, knotless techniques have been developed. There is, however, still room for improvement, for apparatuses and methods that permit the surgery to be performed more quickly and with a more certain and stable result.

SUMMARY

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements In a first separate aspect, the present invention may take the form of a method of attaching target tissue to a pilot hole in a bone that uses a suture assembly having a distal and a proximal end, and including a suture length having a first portion, which terminates coincident to the distal end of the suture assembly, and a second portion, which is formed into a slip knot about the first portion, and an anchor sleeve, slidingly engaged to the suture length, and co-located with the slip knot, the suture length being doubled upon itself, wherein first and second portions are adjacent and form a loop and a loop end where the suture length undergoes a U-bend, the loop end being coincident to the proximal end of the suture assembly. In the method, the adjacent first and second portions are passed about the target tissue and the loop end is passed about the distal end, so that a cinchable loop is formed from the loop end to where the first and second portions pass through the loop end. Then, the cinchable loop is cinched about the target tissue and the slip knot and anchor sleeve are slid, until they are adjacent to the target tissue. Finally, the slip knot and anchor sleeve are pushed into the pilot hole.

In a second separate aspect, the present invention may take the form of a method of attaching target tissue to a pilot hole in a bone that utilizes a suture assembly having an anchor sleeve; a sliding suture, having a first end and a second end, and passing through the anchor sleeve; and a shuttle having a shuttle loop and a free end, opposed to the shuttle loop, and passing through the anchor sleeve, with the free end and the shuttle outside of the anchor sleeve. In the method, the sliding suture is passed about the target tissue and the first end is engaged to the shuttle loop. Then, the anchor sleeve is pushed into the pilot hole, and the free end is pulled to pull the shuttle into the anchor sleeve in the pilot hole, thereby setting the anchor sleeve into the pilot hole.

In a third separate aspect, the present invention may take the form of a method of connecting two pieces of tissue that utilizes a repair assembly, which includes a repair piece, having a finger trap sleeve, a repair loop in fixed relationship to the sleeve and attached to a first end of the sleeve, and a repair strand extending out of a second side of the sleeve, opposed to the first end of the sleeve, the repair strand terminating in a repair strand free end; and a shuttle, including a shuttle loop and a shuttle strand that extends from the shuttle loop and passes through the sleeve, and terminating in a shuttle strand free end. In the method, the shuttle loop and the repair strand free end are passed through both of the two pieces of tissue, so that the repair loop and shuttle strand free end are separated from the shuttle loop and repair strand free end by the two pieces of tissue. Then, the repair strand free end is threaded through the repair loop and the shuttle loop, consecutively. The shuttle strand free end is pulled, thereby pulling the repair loop through the piece of tissue. Finally, the shuttle is pulled entirely free of the repair piece, and leaving the repair piece, looping through and about the two pieces of tissue, with the finger trap sleeve adjacent to the two pieces of tissue and the portion of the repair strand trapped in the finger trap sleeve.

BRIEF DESCRIPTION OF DRAWINGS

Various embodiments of the invention are disclosed in the following detailed description and accompanying drawings.

FIG. 10D is a side view of a suture assembly, similar to that of FIG. 10A, but with yet another different slip knot and sleeve configuration.

FIG. 10E is a side view of a suture assembly, similar to that of FIG. 10A, but with still another different slip knot and sleeve configuration.

DETAILED DESCRIPTION AND EMBODIMENTS

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

Figure 1:
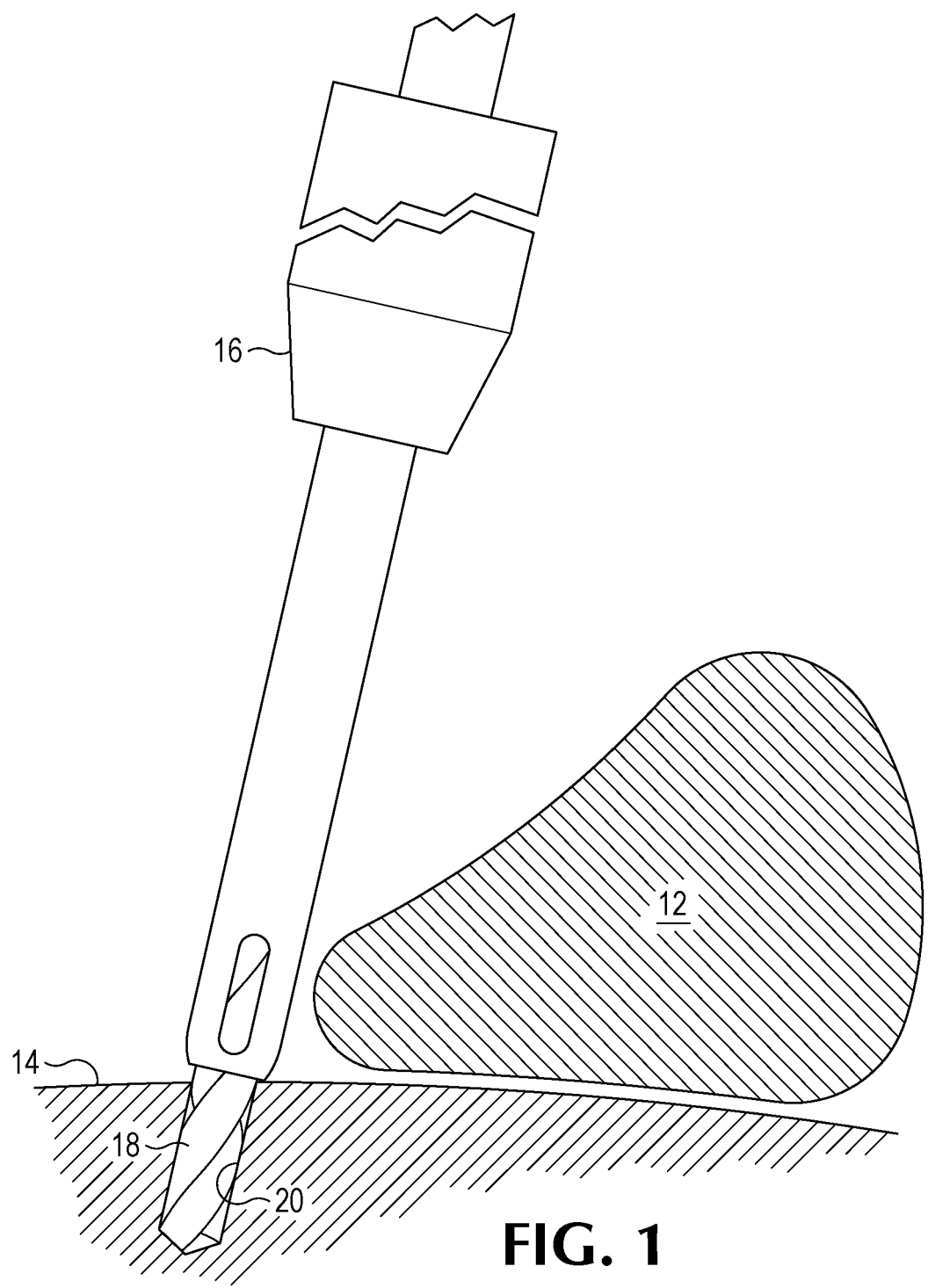
FIG. 1 is a side view of a drill creating a hole in bone, as a first step in a method for the attachment of soft tissue to bone.
Figure 2:
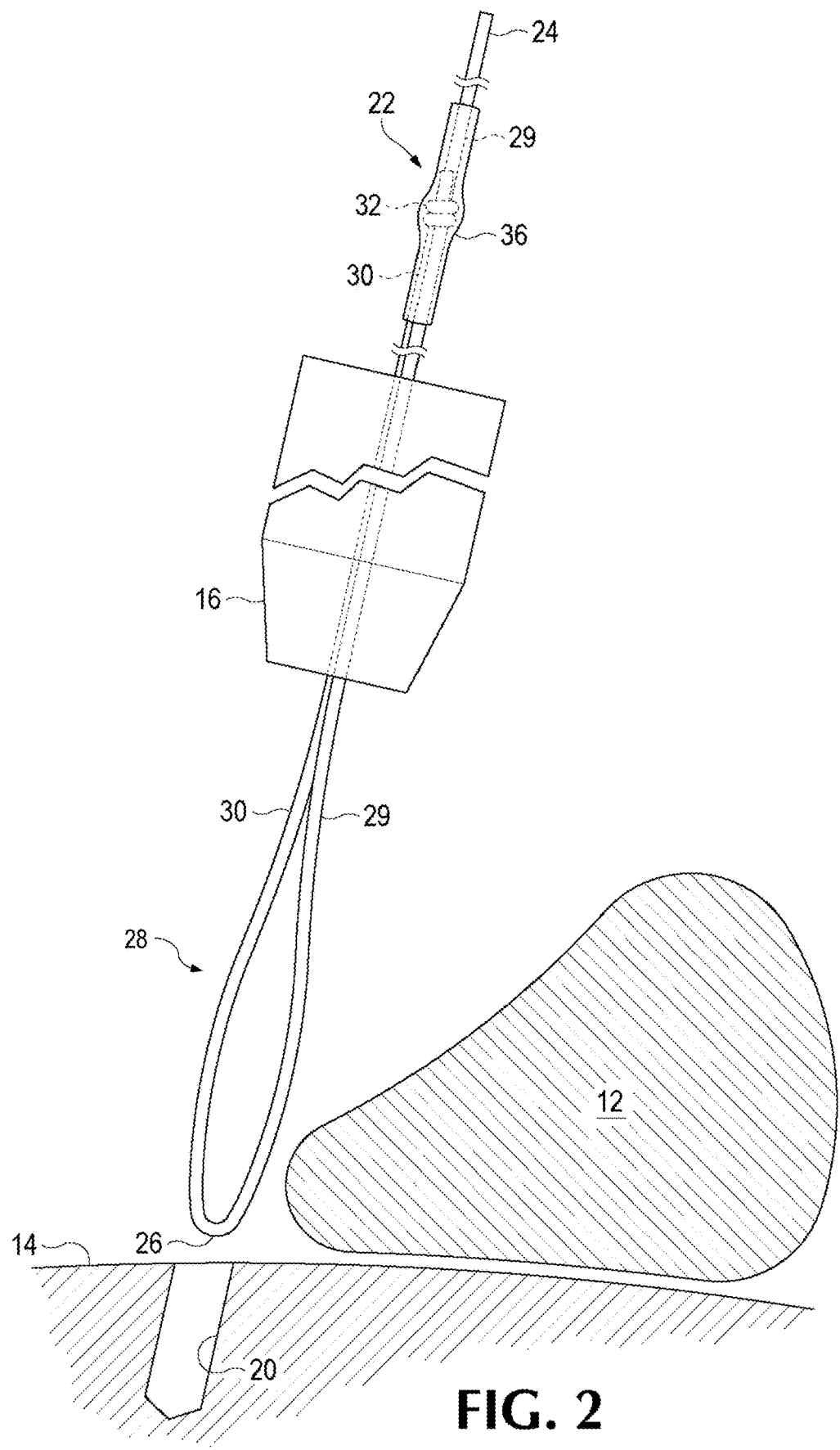
FIG. 2 is a side view of a suture assembly being introduced through a cannulated instrument into the operation theater, as a second step in a method for the attachment of soft tissue to bone

In a first preferred embodiment, target tissue 12 is tied to a nearby bone 14, utilizing in part a canula tool 16, which is first used to introduce a drill 18 to create a pilot hole 20 in bone 14. Referring, now, to FIG. 2 a suture assembly 22, having a distal end 24 and a proximal end 26, includes a suture length 28, having a first portion 29 that terminates in a location coincident to the distal end 24 of the assembly 22. Suture length 28 is doubled up upon itself, thereby forming a loop end that is coincident with the proximal end 26 of assembly 22. A second portion 30 of suture length is formed into a slip knot 32 about the first portion 29. Slip knot 32 is positioned within the lumen of a braided suture 36, that forms an anchor sleeve.

Figure 3:
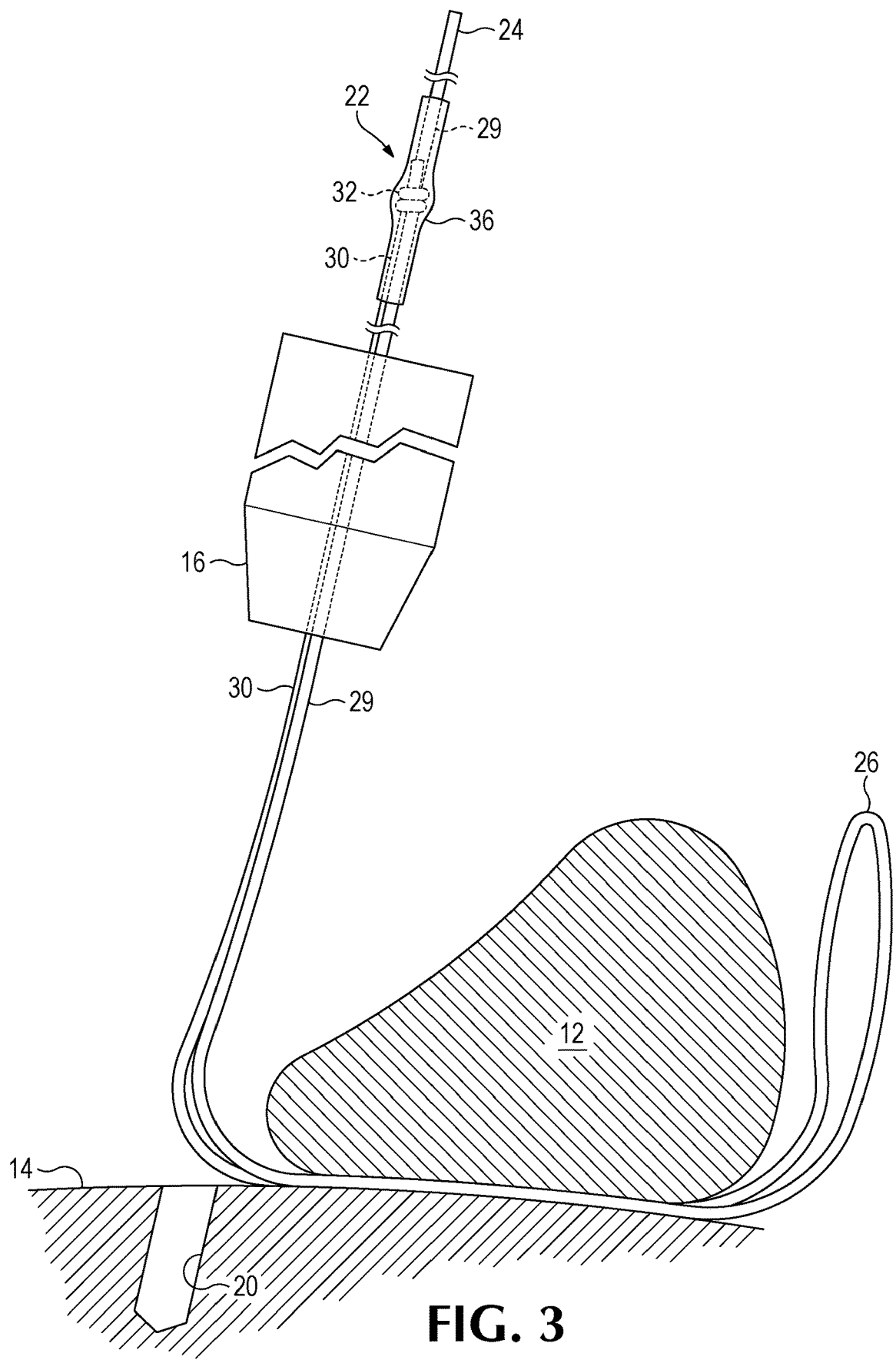
FIG. 3 is a side view of the suture assembly being wrapped about soft tissue, as a third step in a method for the attachment of soft tissue to bone
Figure 4:
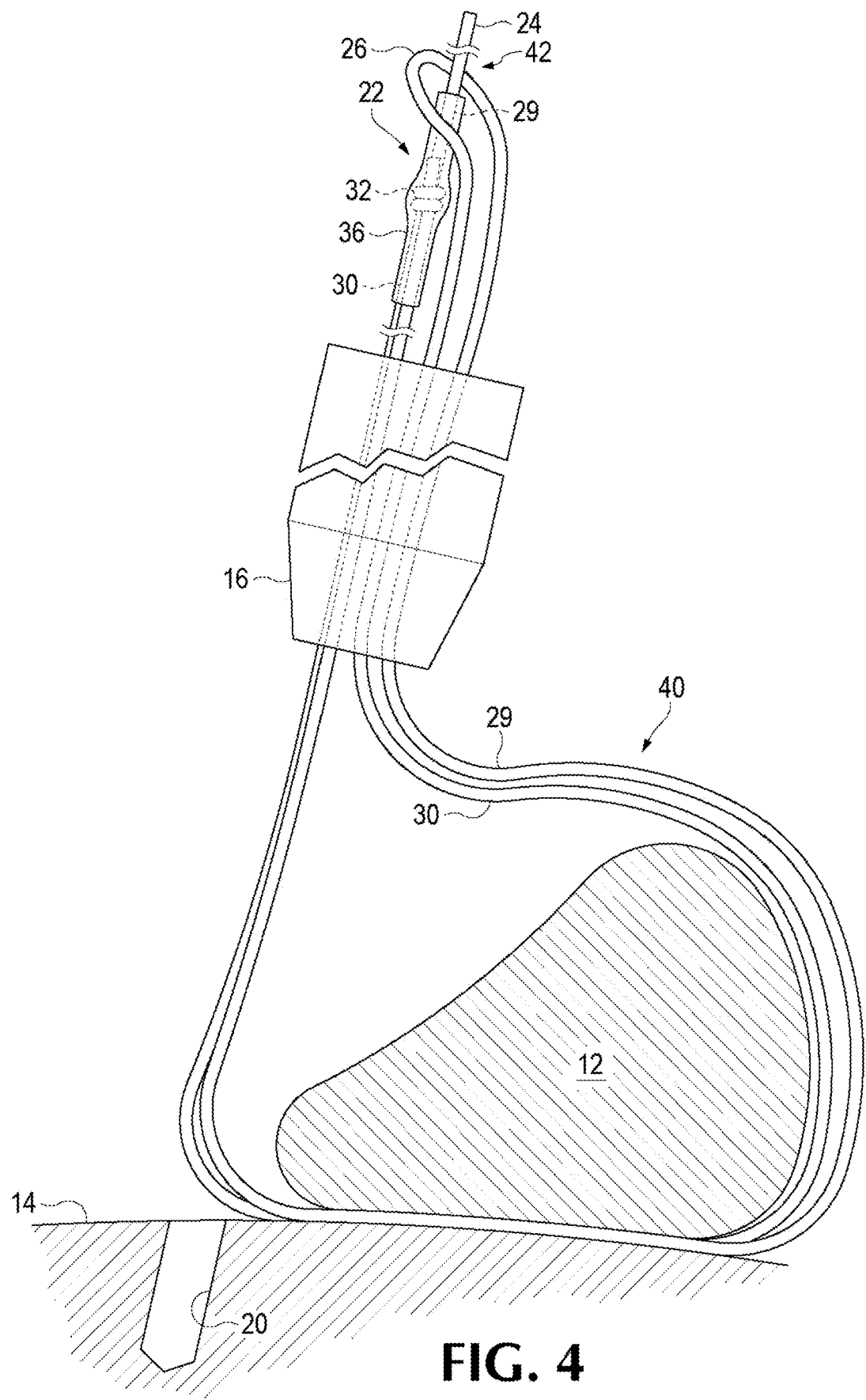
FIG. 4 is a side view of the suture assembly being formed into a loop, as a fourth step in a method for the attachment of soft tissue to bone
Figure 5:
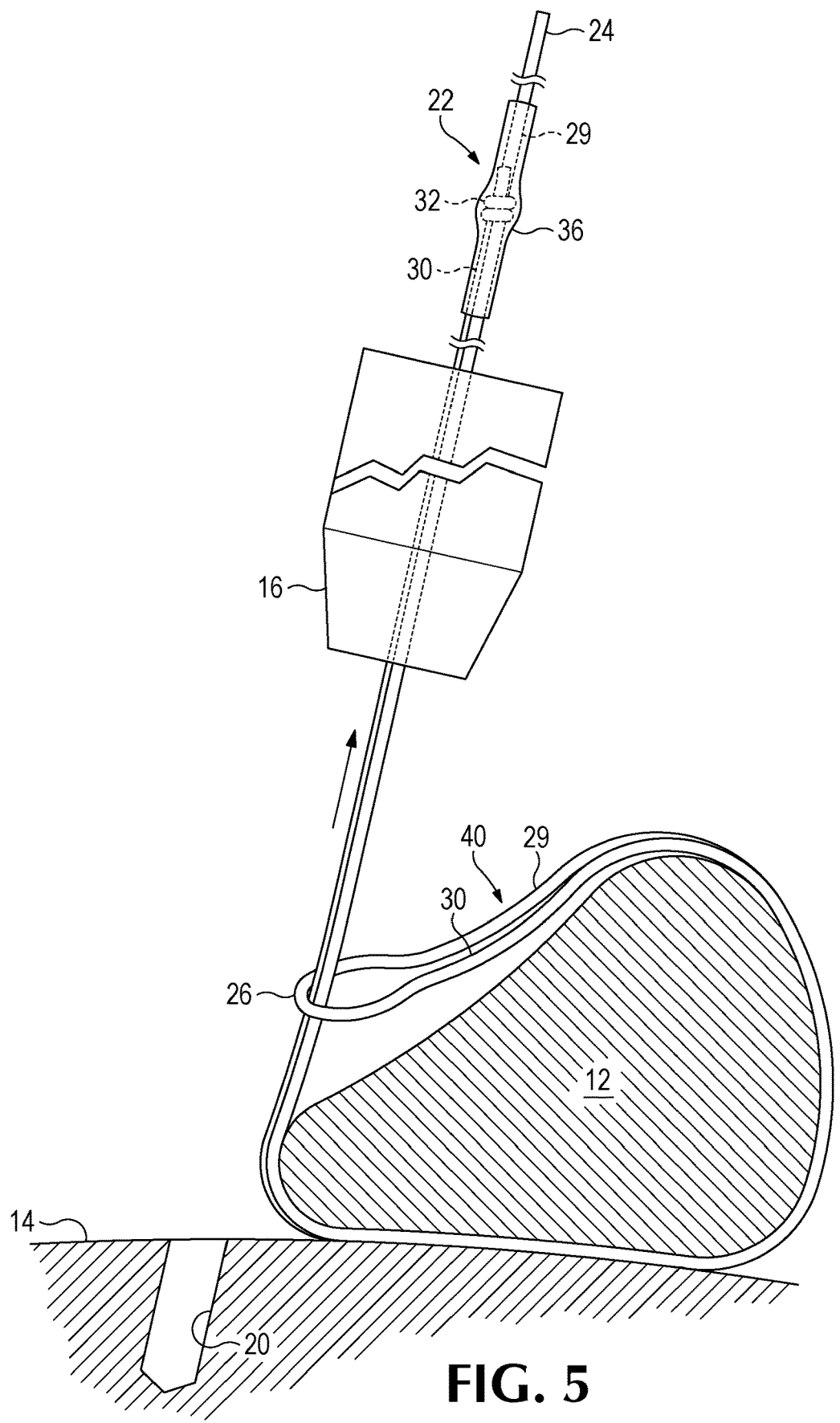
FIG. 5 is a side view of the suture assembly, formed into a loop that is being cinched up around soft tissue, as a fifth step in a method for the attachment of soft tissue to bone
Figure 6:
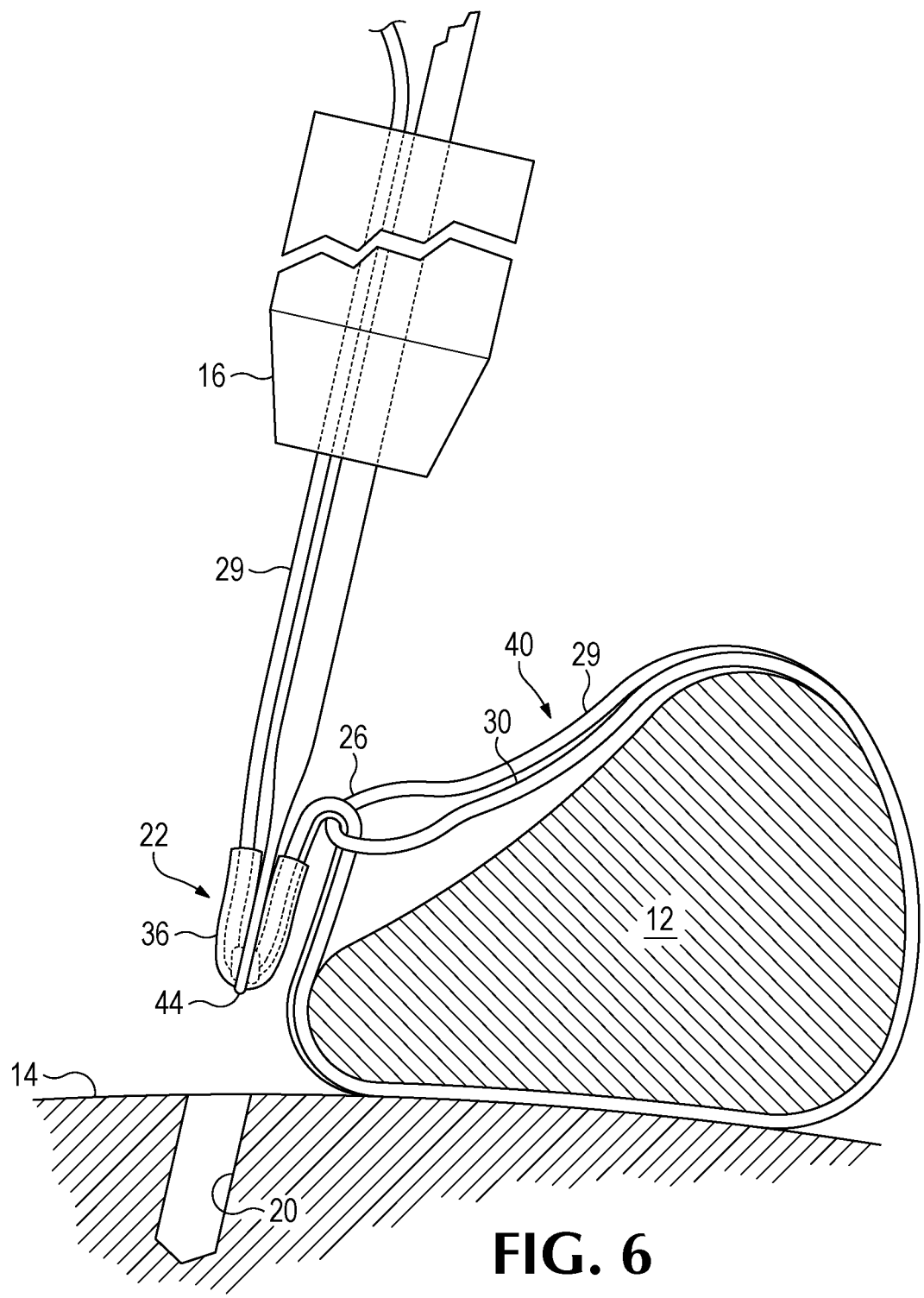
FIG. 6 is a side view of an insertion tool engaged with the suture assembly and aimed at the hold created in FIG. 1, as a sixth step in a method for the attachment of soft tissue to bone
Figure 7:
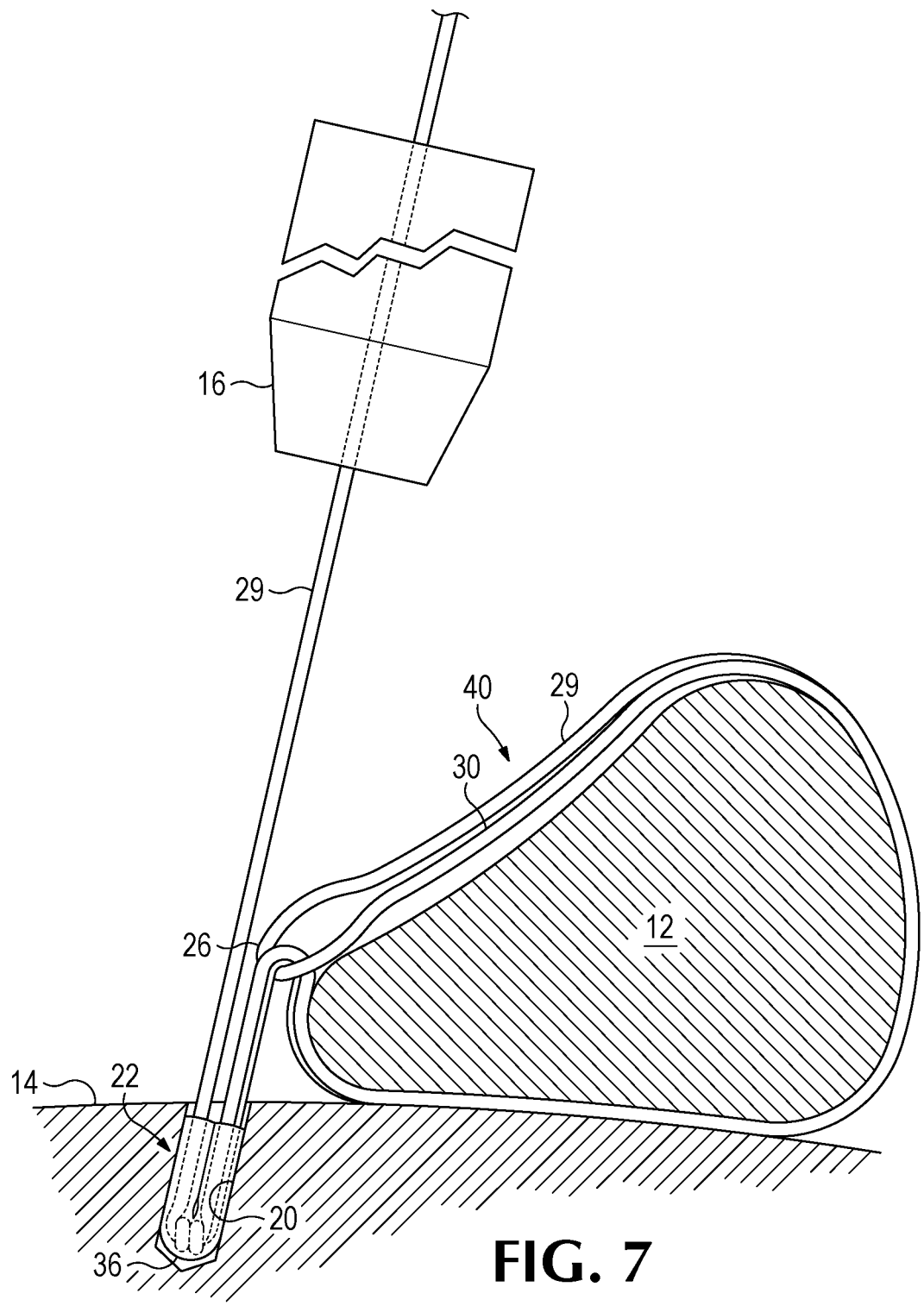
FIG. 7 is a side view of the suture assembly, a portion of which has been pushed into the bone hole, being further cinched around the soft tissue, as a seventh step in a method for the attachment of soft tissue to bone
Figure 8:
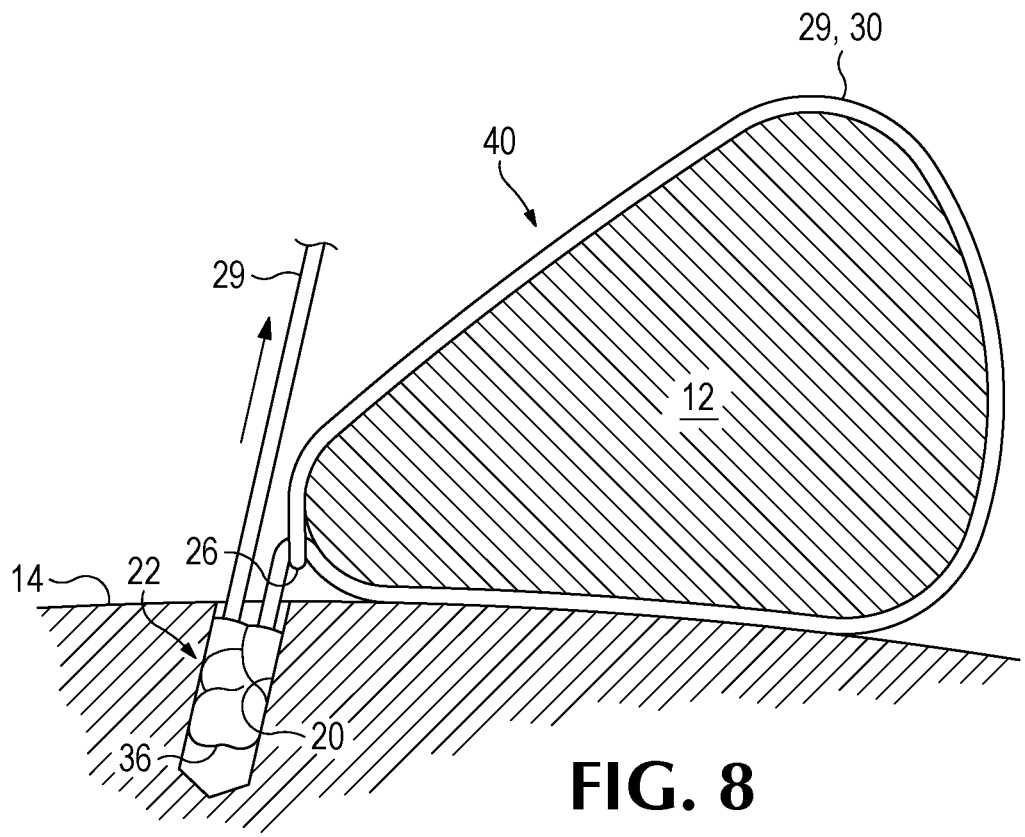
FIG. 8 is a side view of the suture assembly, now cinched tightly about the soft tissue, and with the portion pushed into the bone hole, with a portion now being pulled to securely anchor it in the bone hole.
Figure 9:
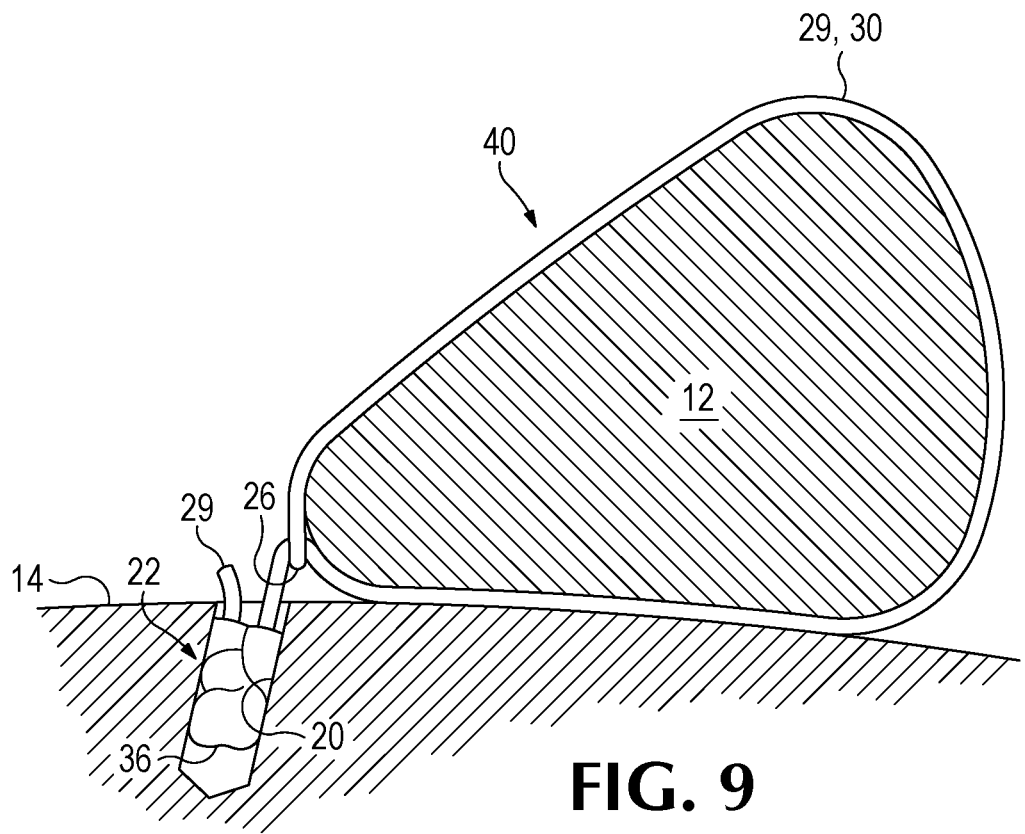
FIG. 9 is a side view of the suture assembly, with a portion cut off.

Referring to FIG. 3, proximal end 26 is brought around a portion of target tissue 12 and, referring to FIG. 4, looped over the distal end 24 of the suture assembly 22, thereby forming a cinchable loop 40, that extends from proximal end 26, around target tissue 12, and up to the point 42 where first portion 29 extends past proximal end 26. Next, referring to FIGS. 5 and 6, the loop 40 is cinched up by pulling on the distal end 24 of assembly 22, and introducer 44 is used to push anchor sleeve 36, and included slip knot 32, into pilot hole 20. As shown in FIGS. 7-9, introducer tool 44 is removed, first portion 29 is pulled, setting anchor sleeve 36 into pilot hole 20, and the remainder of first portion 29 is trimmed off, leaving a knotless binding of target tissue 12 to bone 14.

Figure 10A:
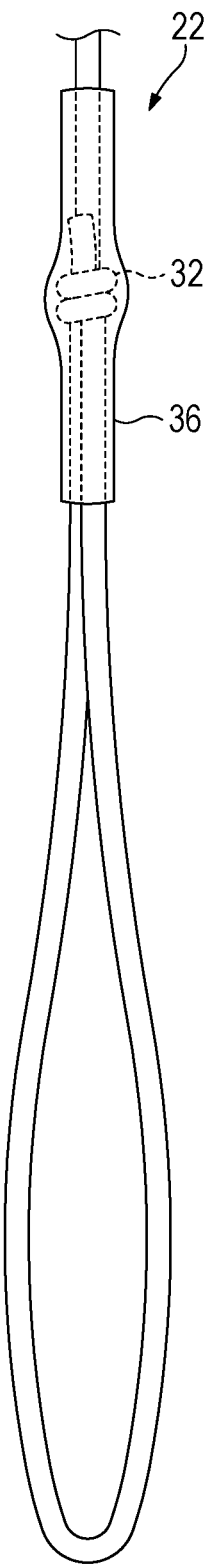
FIG. 10A is a side view of the suture assembly of FIG. 2.
Figure 10B:
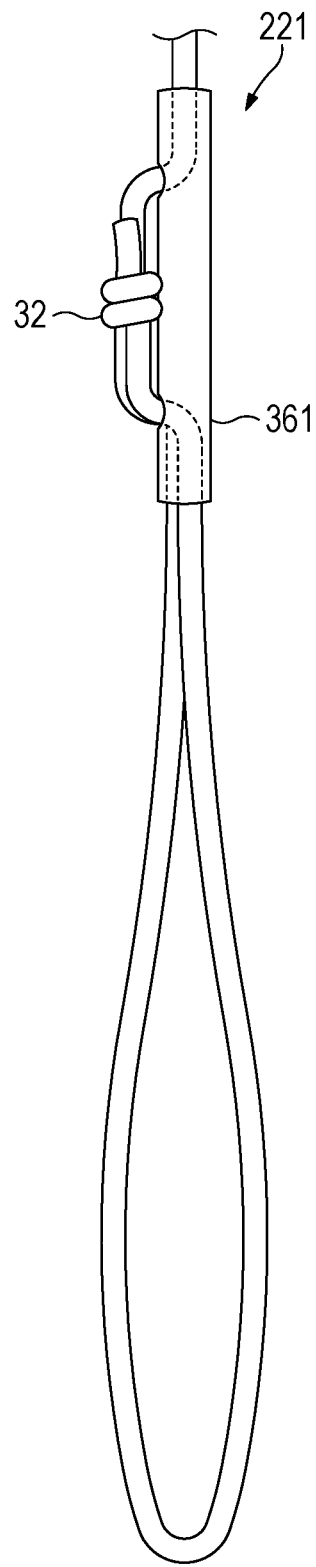
FIG. 10B is a side view of a suture assembly, similar to that of FIG. 10A, but with a different slip knot and sleeve configuration.
Figure 10C:
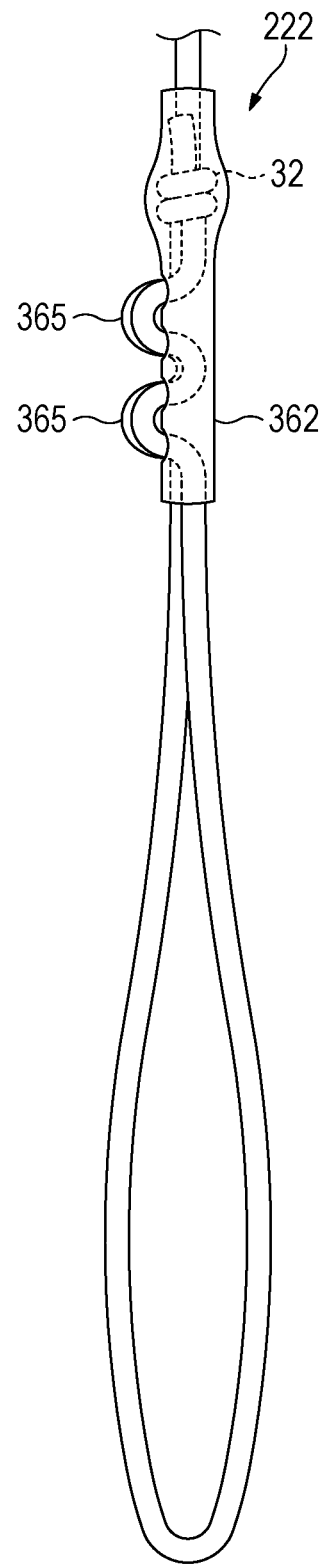
FIG. 10C is a side view of a suture assembly, similar to that of FIG. 10A, but with another different slip knot and sleeve configuration.
Figure 11:
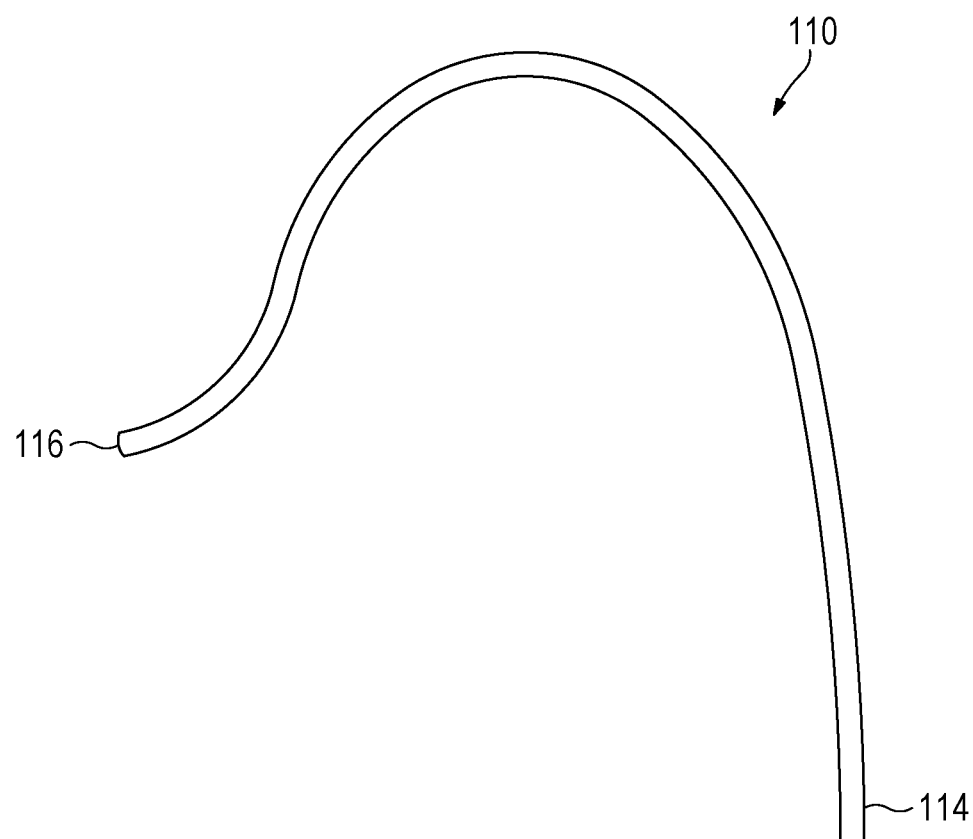
FIG. 11 is a side view of an alternative suture assembly.
Figure 11:
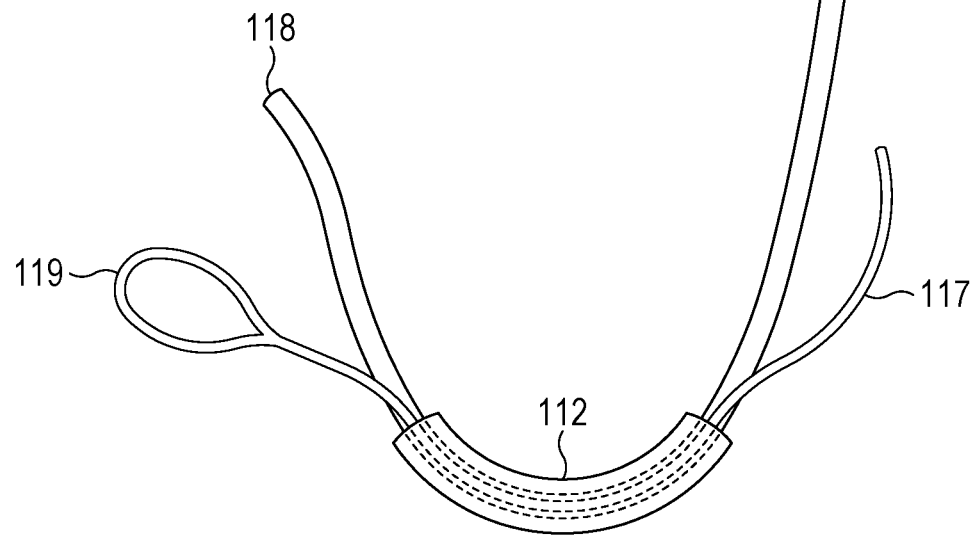

Referring, now, to FIGS. 10A-10E, a number of variants of assembly 22 are shown, having differences in the anchor sleeve 36 and slip knot 32 arrangement. FIG. 10B shows assembly 221, in which, going from distal end to proximal end, first portion 29 enters the distal end of anchor sleeve 361, broaches out of anchor sleeve 361, where it is joined by second portion 30, tied in slip knot 32, and then broaches into anchor sleeve 361 before exiting the proximal end of the lumen of anchor sleeve 361. FIG. 10C shows assembly 222, in which, again from distal end to proximal end, first portion 29 enters anchor sleeve 362, is joined by second portion 30 tied in a slip knot 32 about portion 29, and then broaches back and forth out of and into anchor sleeve 362, forming two undulations 365 out of anchor sleeve 362, before reentering and exiting out of the lumen proximal end. The undulations 365 help to set anchor firmly into pilot hole 20. Other numbers of undulations 365 are possible. In FIGS. 10D and 10E assemblies 223 and 224 are the same as assembly 22, except for that in assembly 223 slip knot 32 is held in place with a spot of glue 366 and in assembly 224, slip knot 32 is held in place with a stitch 367.

Figure 12:
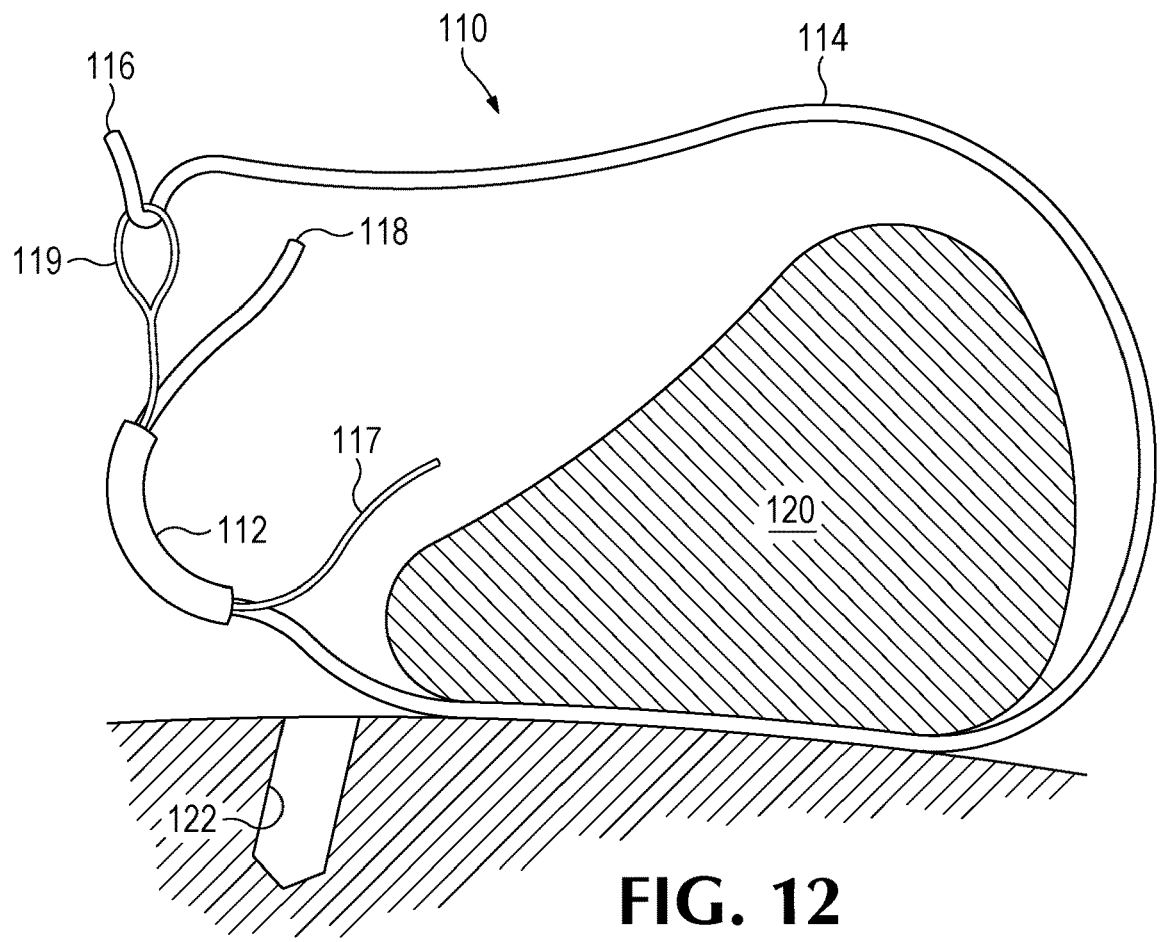
FIG. 12 is a side view of the alternative suture assembly of FIG. 11, in a first stage of its deployment attaching soft tissue to bone.
Figure 13:
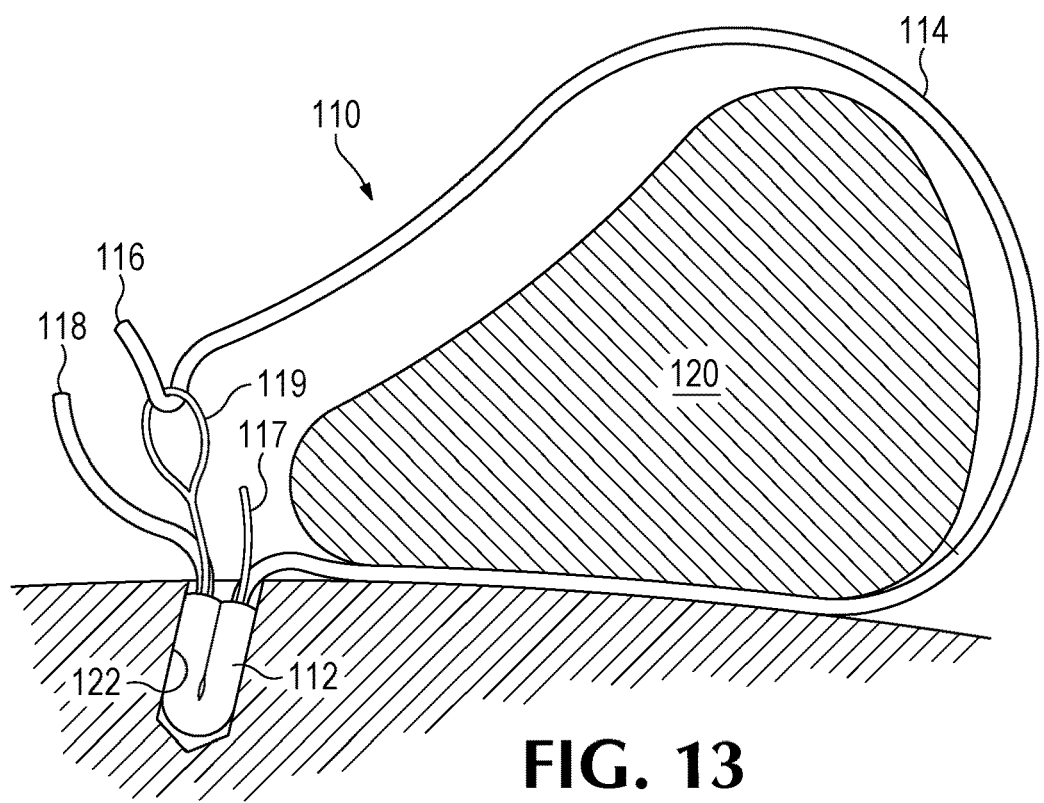
FIG. 13 is a side view of the alternative suture assembly of FIG. 11, in a second stage of its deployment attaching soft tissue to bone.
Figure 14:
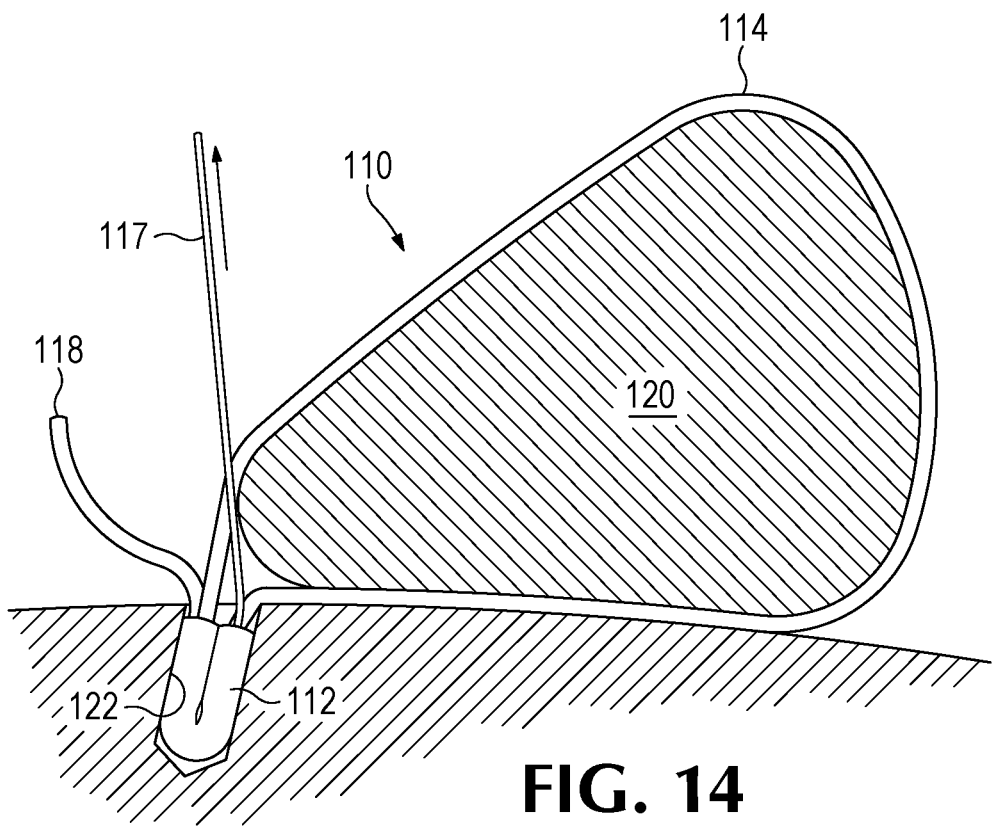
FIG. 14 is a side view of the alternative suture assembly of FIG. 11, in a third stage of its deployment attaching soft tissue to bone.
Figure 15:
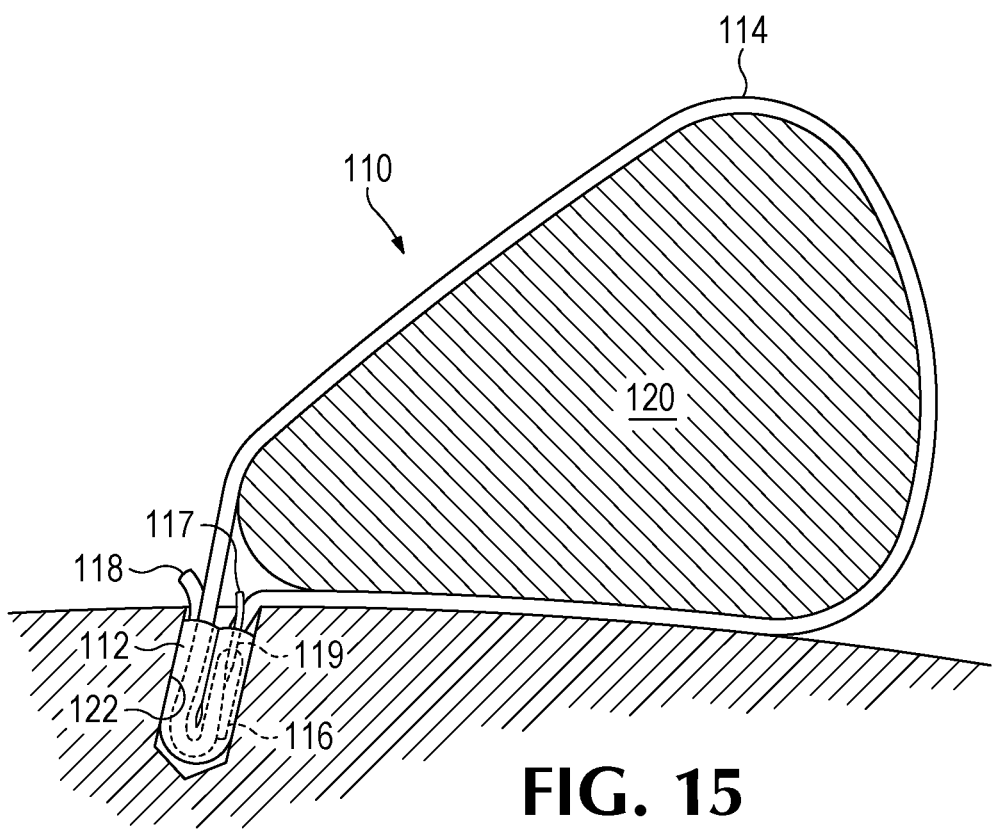
FIG. 15 is a side view of the alternative suture assembly of FIG. 11, in the final stage of its deployment attaching soft tissue to bone.
Figure 16:
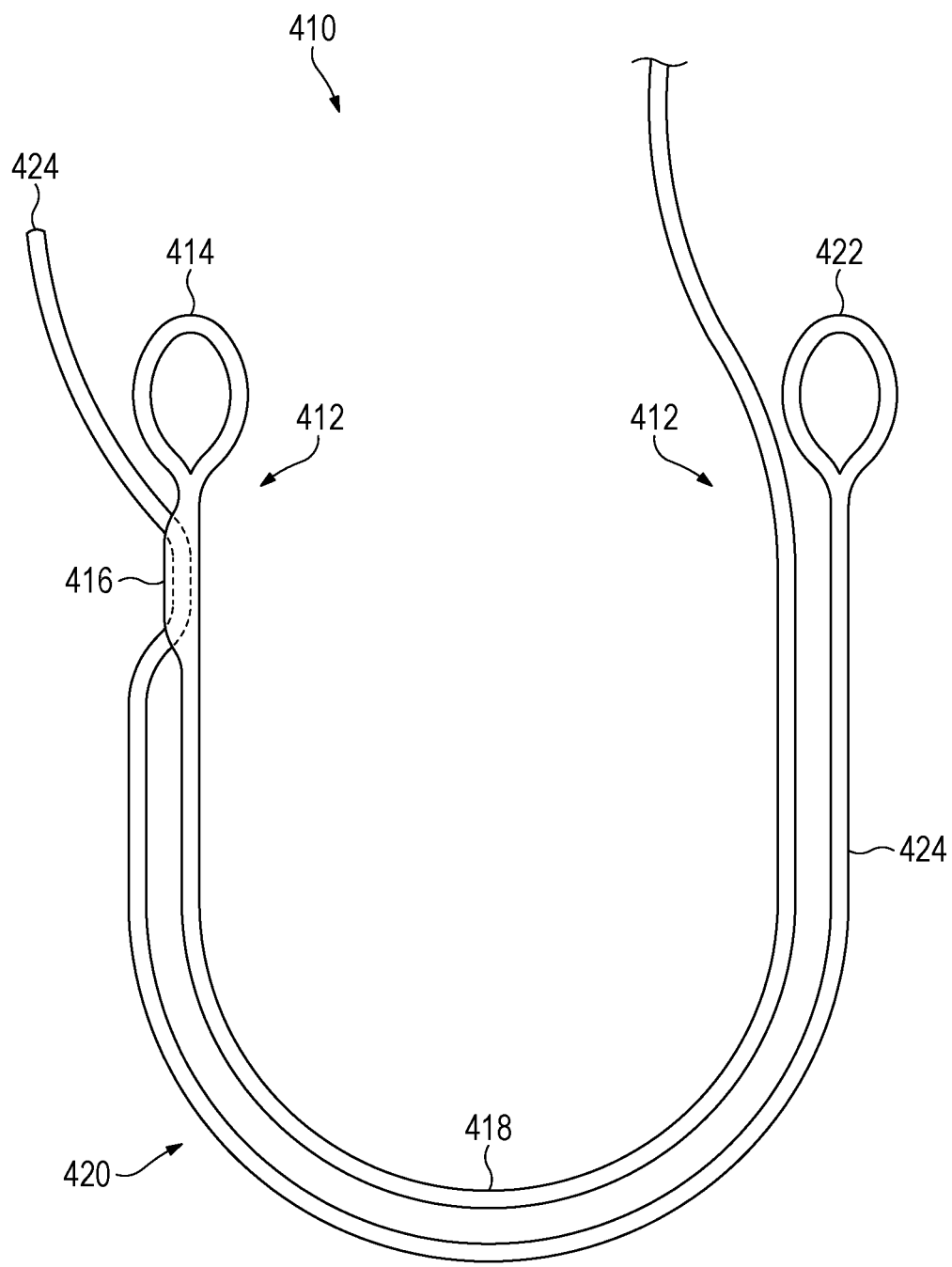
FIG. 16 is a side view of another alternative suture assembly.

Referring to FIGS. 11-15, in a second preferred embodiment an anchored-loop forming assembly 110 is provided, including an anchor sleeve 112, and a sliding suture 114 having a first end 116 and a second end 118. Also, a shuttle 117 is engaged through sleeve 112 and includes a shuttle loop 119. Referring to FIG. 12, the method begins with the positioning of suture 114 about a portion of target tissue 120, and the engagement of the first end 116 to the shuttle loop 119 introduction of sleeve 112 into a pilot hole 122. (At this point, the pilot hole 122 has already been drilled). The anchor sleeve 112 is pushed into the pilot hole 122 (using a tool similar to introducer tool 44, shown in FIG. 6). As shown in FIG. 14, the free end of shuttle 117 is pulled to pull shuttle loop 119 into anchor sleeve, where it acts to thicken anchor sleeve 112, setting it into pilot hole 122 and the stray ends of suture 114 and shuttle 117 are cut (as shown in FIG. 15). The second embodiment utilizes the same sort of cannulated instrument 16 as shown in the figures describing the first embodiment. In one embodiment the shuttle loop 119 is made of a metal, such as nitinol that is roughened so that said implantable tail physically engages to said shuttle loop 119. In this embodiment the shuttle 117 may be made of metal, such as nitinol.

In both the first and second embodiments, target tissue 12, 120 is typically pierced with a needle, to pull the suture about it. One application of these described methods/embodiments is the reattachment of the labrum to the glenoid, in the shoulder of a patient.

Figure 17:
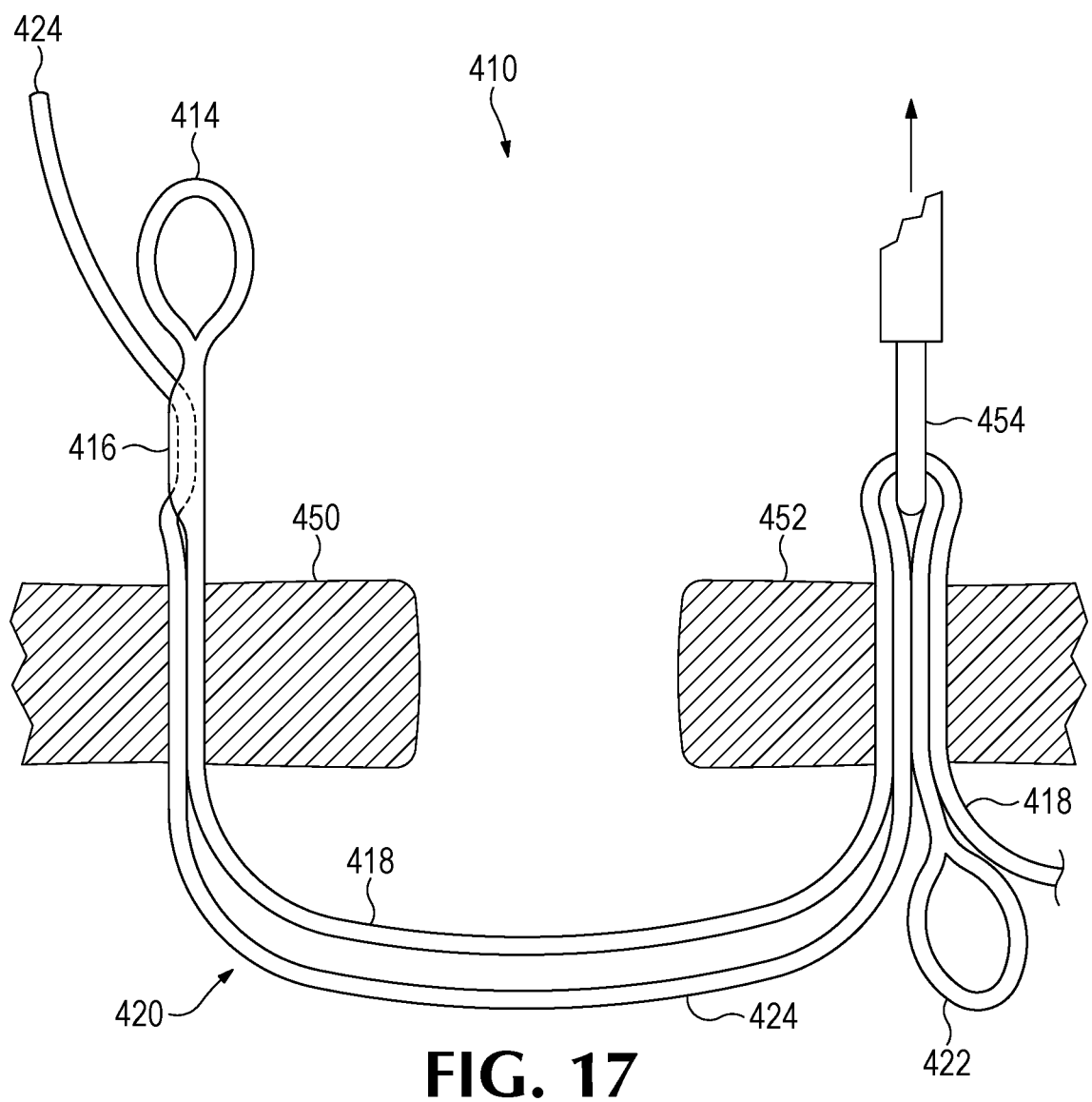
FIG. 17 is a side view of the alternative suture assembly of FIG. 16, in a first stage of its deployment attaching soft tissue to bone.
Figure 18:
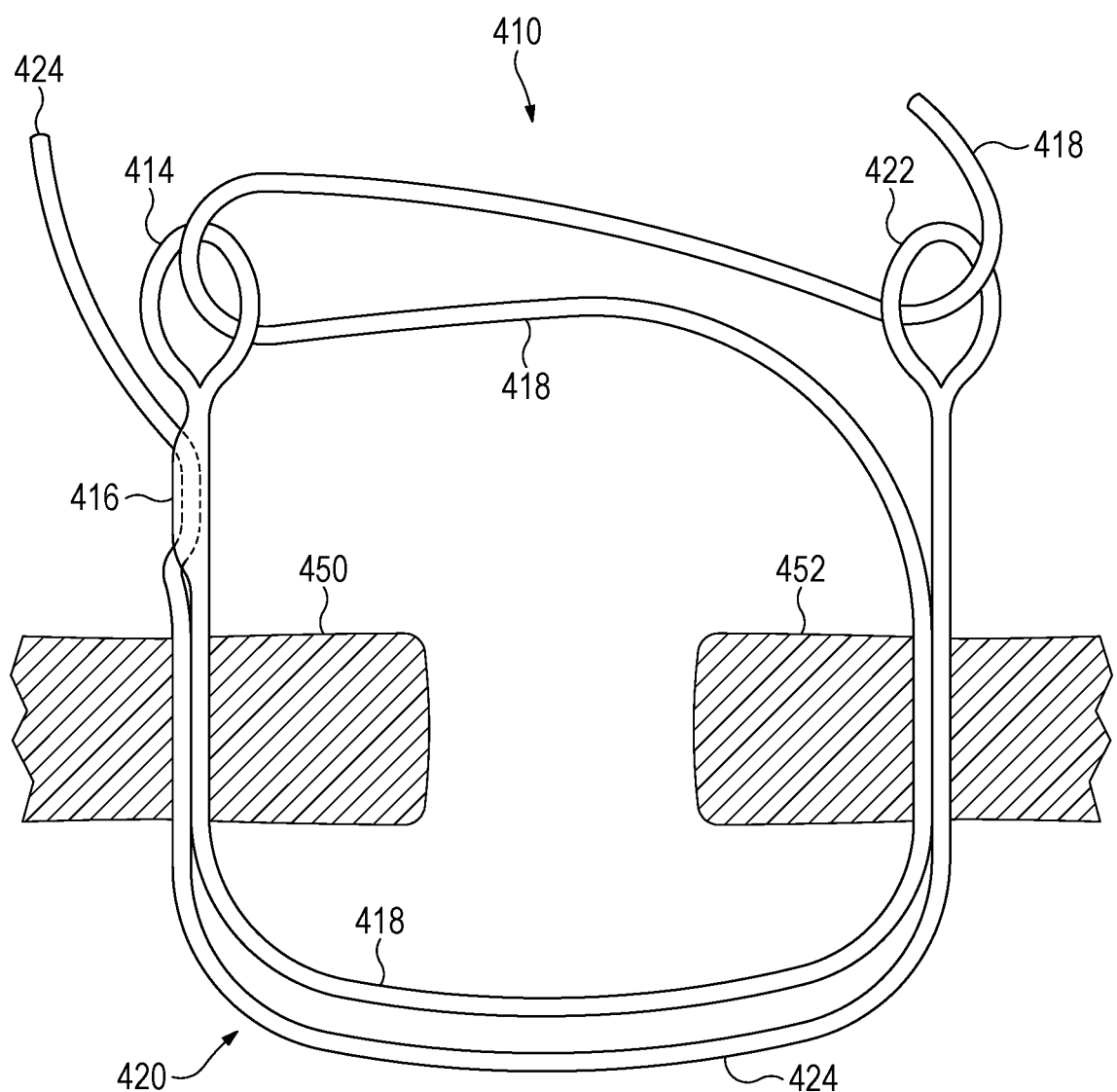
FIG. 18 is a side view of the alternative suture assembly of FIG. 16, in a second stage of its deployment attaching soft tissue to bone.
Figure 19:
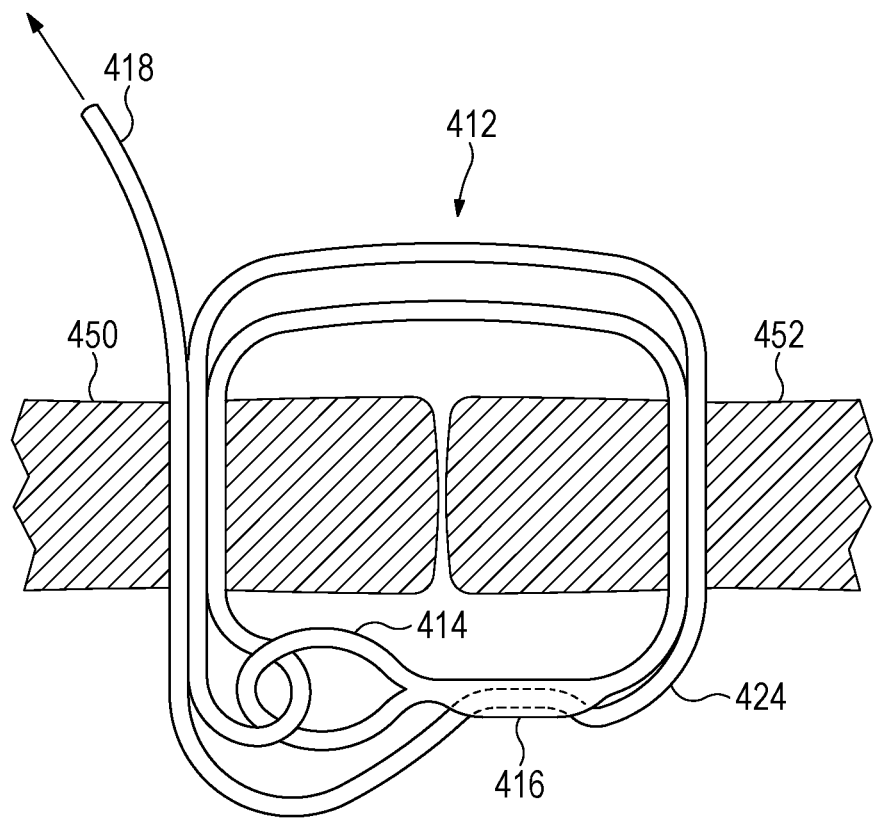
FIG. 19 is a side view of the alternative suture assembly of FIG. 16, in a third stage of its deployment attaching soft tissue to bone.
Figure 20:
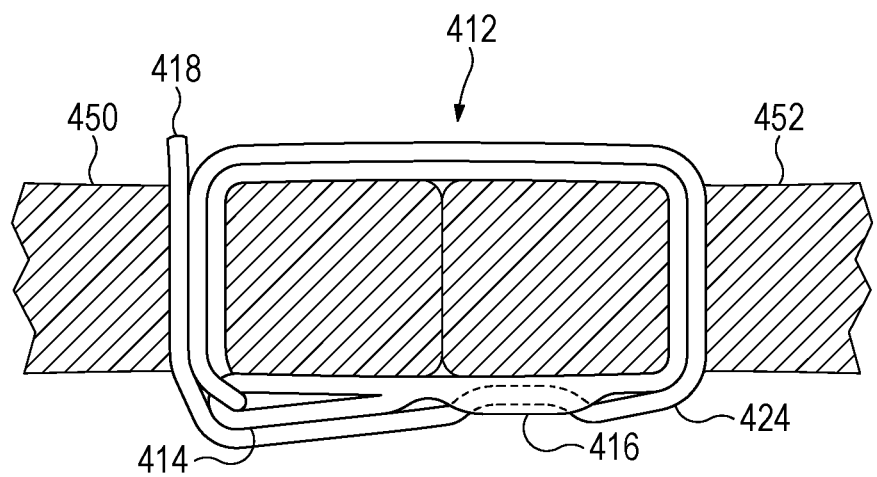
FIG. 20 is a side view of the alternative suture assembly of FIG. 16, in the final stage of its deployment attaching soft tissue to bone.

Referring to FIGS. 16-20, in a third embodiment and method, a construct 410, includes an implantable part 412, including a loop, 414, connected to a sleeve 416, which is connected to implantable tail 418. Engaged with implantable part 412 is a shuttle 420, including a shuttle loop 422, attached to a shuttle tail 424. Tails 418 and 424 are made of suture material. Referring to FIG. 17, construct 410 has been engaged to two sections of tissue 450 and 452, using a suture passer 454. Suture passer 454 may be, for example, the NanoPass, available from Stryker Corporation, which maintains a website at www.stryker.com. Referring to FIG. 18, implantable tail 418 is engaged through implantable loop 414 and shuttle loop 422. The shuttle tail 424 is pulled, thereby as shown in FIG. 19, pulling implantable loop 414 and sleeve 416 through tissue 452; pulling implantable tail 418 through sleeve 416 and tissue 450 and pulling shuttle 420 completely out of the construct 410. Implantable loop 414 is thereby formed into a loop holding tissues 450 and 452, together. Tail 418 is then pulled further, and as shown in FIG. 20, implantable part 412 is cinched tight, to better hold tissues 450 and 452 together. In one embodiment the shuttle loop 422 is made of a metal, such as nitinol that is roughened so that said implantable tail physically engages to said shuttle loop 422. In this embodiment the shuttle 420 may be made of metal, such as nitinol.

In an alternative embodiment, tissue (such as tissue 450) is attached to bone, by pushing sleeve 416 into a pilot hole in bone, similar to pushing sleeve 112 into pilot hole 122 in FIG. 14, or sleeve 36 into pilot hole 20, in FIG. 9. Then, tail 418 can be pulled to tighten implantable pat 412, to hold tissue 450 to the bone.

The above-described constructs and methods find application, for example, in repairing a tear in the meniscus of the knee joint or reattaching a portion of the labrum to the glenoid in the shoulder joint.

The disclosed embodiments are illustrative, not restrictive. While specific configurations of the suture assemblies and their methods of use have been described, it is understood that the present invention can be applied to a wide variety of apparatuses and methods of repair of tendons and other body tissue. There are many alternative ways of implementing the invention.

What is claimed is:

1. A method of connecting two pieces of tissue, comprising:
    a. providing a repair assembly, including:
        i. a repair piece, having a finger trap sleeve, a repair loop in fixed relationship to said sleeve and attached to a first end of said sleeve, and a repair strand extending out of a second side of said sleeve, opposed to said first end of said sleeve, said repair strand terminating in a repair strand free end;
        ii. a shuttle, including a shuttle loop and a shuttle strand that extends from said shuttle loop and passes through said sleeve, and terminating in a shuttle strand free end; and
    b. passing said shuttle loop and said repair strand free end through both of said two pieces of tissue, so that said repair loop and shuttle strand free end are separated from said shuttle loop and repair strand free end by said two pieces of tissue;
    c. threading said repair strand free end through said repair loop and said shuttle loop, consecutively;
    d. pulling on said shuttle strand free end, and thereby pulling said repair loop through a said piece of tissue;
    e. pulling said shuttle entirely free of said repair piece, and leaving said repair piece, looping through and about said two pieces of tissue, with said finger trap sleeve adjacent to said two pieces of tissue and said a portion of said repair strand trapped in said finger trap sleeve.

2. The method of claim 1, wherein said shuttle loop is made of comprises nitinol.

3. The method of claim 2, wherein at least a portion of the said shuttle loop comprises a roughened surface.

4. The method of claim 1, wherein said two pieces of tissue comprises at least a portion of the meniscus of the knee joint and have been mutually separated by a tear.

5. The method of claim 1, wherein said two pieces of tissue comprise at least a portion of a glenoid and at least a portion of a labrum.

6. The method of claim 1, wherein said step of pulling said shuttle entirely free of said repair piece induces said two pieces of tissue to move toward each other.

7. The method of claim 1, wherein said step of pulling said shuttle entirely free of said repair piece engages said two pieces of tissue together.

8. The method of claim 1, wherein said repair piece further comprises an implantable tail and said shuttle loop further comprises a shuttle tail.

9. The method of claim 8, wherein said implantable tail or said shuttle tail comprises a suture material.

10. The method of claim 8, wherein said implantable tail and said shuttle tail comprise a suture material.

* * * * *